US012678520B2

(12) United States Patent
Tsai et al.

(10) Patent No.: US 12,678,520 B2
(45) Date of Patent: Jul. 14, 2026

(54) MICROBIAL INHIBITION DEVICE

(71) Applicant: NATIONAL APPLIED RESEARCH LABORATORIES, Taipei City (TW)

(72) Inventors: Hsin-Yi Tsai, Taipei City (TW);
Yu-Hsuan Lin, Taipei City (TW);
Chun-Han Chou, Taipei City (TW);
Kuo-Cheng Huang, Taipei City (TW);
Ching-Ching Yang, Taipei City (TW)

(73) Assignee: NATIONAL APPLIED RESEARCH LABORATORIES, Taipei City (TW)

( * ) Notice: Subject to any disclaimer, the term of this patent is extended or adjusted under 35 U.S.C. 154(b) by 705 days.

(21) Appl. No.: 18/104,279

(22) Filed: Jan. 31, 2023

(65) Prior Publication Data

US 2024/0000983 A1    Jan. 4, 2024

(30) Foreign Application Priority Data

Jul. 4, 2022    (TW) ................................. 111125016

(51) Int. Cl.
A61L 2/03 (2026.01)
A61L 2/24 (2006.01)
(Continued)

(52) U.S. Cl.
CPC ..................................... A61L 2/03 (2013.01);
A61L 2/24 (2013.01); H02S 20/26 (2014.12);
H02S 40/38 (2014.12); A61L 2202/14
(2013.01)

(58) Field of Classification Search
CPC .......... A61L 2/03; A61L 2/24; A61L 2202/14;
H02S 20/26; H02S 40/38
See application file for complete search history.

(56) References Cited

U.S. PATENT DOCUMENTS

| | | |
|---|---|---|
| 7,892,486 B2 | 2/2011 | Mizuno et al. |
| 8,652,403 B2 | 2/2014 | Reddy et al. |
| | (Continued) | |

FOREIGN PATENT DOCUMENTS

| | | |
|---|---|---|
| CN | 1329679 A | 1/2002 |
| CN | 101156575 A | 4/2008 |
| | (Continued) | |

OTHER PUBLICATIONS

English translation of CN106132137 (Year: 2016).*

(Continued)

*Primary Examiner* — Regina M Yoo
(74) *Attorney, Agent, or Firm* — Cheng-Ju Chiang

(57) ABSTRACT

A microbial inhibition device for inhibiting microorganisms on a predetermined object includes: a covering member covering the predetermined object, and having an attachment surface for attaching to the predetermined object, and an exposed surface opposite to the attachment surface, wherein the covering member includes at least a conductive medium layer, and the conductive medium layer constitutes a predetermined area of the exposed surface; a control module configured to issue a control command reflecting a predetermined conduction mode; and a power supply module electrically connected to the conductive medium layer, and configured to receive the control command so as to power the conductive medium layer according to the predetermined conduction mode based on the control command. The conductive medium layer is conducted with current according to the predetermined conduction mode through the power supply module. Accordingly predetermined microorganisms on the predetermined area are inhibited or killed.

18 Claims, 8 Drawing Sheets

(51) Int. Cl.
   *H02S 20/26*       (2014.01)
   *H02S 40/38*       (2014.01)

(56)            References Cited

U.S. PATENT DOCUMENTS

| | | | |
|---|---|---|---|
| 9,662,411 | B2 | 5/2017 | Rizzone |
| 2011/0070624 | A1 | 3/2011 | Sun et al. |
| 2018/0207301 | A1* | 7/2018 | Beyenal ............... A61N 1/0468 |
| 2023/0126650 | A1* | 4/2023 | Samardzija ........... H01Q 1/007 340/572.8 |
| 2023/0363473 | A1* | 11/2023 | Topsakal ................ A41D 13/11 |

FOREIGN PATENT DOCUMENTS

| | | | |
|---|---|---|---|
| CN | 101879318 | A | 11/2010 |
| CN | 201832180 | U | 5/2011 |
| CN | 204261067 | U | 4/2015 |
| CN | 204442817 | U | 7/2015 |
| CN | 205548503 | U * | 9/2016 |
| CN | 106132137 | A * | 11/2016 ........... H05K 9/0049 |
| CN | 209373134 | U * | 9/2019 |
| CN | 110492021 | A * | 11/2019 ............. B60L 50/64 |
| CN | 111379005 | A * | 7/2020 ........... C25D 17/004 |
| EP | 3400795 | A1 * | 11/2018 ............. A01M 1/22 |
| JP | 4815170 | B2 | 11/2011 |
| KR | 20220069746 | A * | 5/2022 ......... F21V 33/0064 |
| TW | M352255 | U | 3/2009 |
| TW | I522133 | B | 2/2016 |
| TW | M541866 | U | 5/2017 |
| TW | I612981 | B | 2/2018 |
| TW | 202206114 | A | 2/2022 |
| WO | 98/09667 | A1 | 3/1998 |

OTHER PUBLICATIONS

English translation of CN111379005 (Year: 2020).*
English translation of CN205548503 (Year: 2016).*
English translation of KR20220069746 (Year: 2022).*

* cited by examiner

60

MICROBIAL INHIBITION DEVICE

FIELD

The present invention relates to a microbial inhibition device. Specifically, the present invention relates to a microbial inhibition device having a covering member configured to cover a predetermined object.

BACKGROUND

Along with the pandemic of coronavirus disease (COVID-19) outbreaks around the world, importance of cleaning and disinfection come to light again. In order to inhibit or kill microorganisms such as coronaviruses to improve or ensure hygiene of home environments or public spaces, it is usually necessary to perform cleaning and disinfection to objects (specifically, objects easily and frequently touched by unspecified individuals, such as doorknobs or elevator buttons). The current cleaning and disinfection are approximately classified into chemical disinfection performed by alcohol and sterilized water, and physical disinfection performed by irradiating UV light or heating. However, denaturation or unnecessary chemical reactions will occur on many objects subject to alcohol and sterilized water, or disinfection by UV light or heating; therefore, the objects are damaged or service life thereof is shortened. In addition, some methods of cleaning and disinfection may also have potential hazards to people. For example, someone might get intoxicated due to taking foods after touching sterilized water or eye(s) might be burned by UV light due to carelessly looking it directly. All the aforementioned factors increase uncertainty and risk of cleaning and disinfection. In addition, some ways of disinfection such as UV light and heating are also difficult to be widely performed and to be frequently used due to high costs and energy consumption.

As mentioned above, the current methods of cleaning and disinfection have many defects, so that effective objects, frequency, and time to perform cleaning and disinfection are all restricted. Therefore, it is necessary to develop other devices or ways for cleaning and disinfection that can be widely performed and frequently used. Accordingly, it is possible to further expand effective objects, frequency, and time to perform cleaning and disinfection or to make up for at least a portion of the effective objects, frequency, and time that are difficult to perform cleaning and disinfection in the conventional techniques. As such, convenience and safety in cleaning and disinfection can be further improved.

SUMMARY

Means to Solve the Problem

In order to solve the aforementioned problems, one embodiment according to the present invention provides a microbial inhibition device for inhibiting microorganisms on a predetermined object. The microbial inhibition device includes: a covering member configured to cover the predetermined object, and having an attachment surface for attaching to the predetermined object, and an exposed surface opposite to the attachment surface, wherein the covering member includes at least a conductive medium layer, and the conductive medium layer constitutes a predetermined area of the exposed surface; a control module configured to issue a control command, the control command reflecting a predetermined conduction mode; and a power supply module electrically connected to the conductive medium layer, configured to receive the control command, and configured to power the conductive medium layer based on the control command in accordance with the predetermined conduction mode. The conductive medium layer is conducted with current according to the predetermined conduction mode through the power supply module, so as to inhibit or kill predetermined microorganisms on the predetermined area.

Effects Compared to the Prior Art

The microbial inhibition device provided by embodiments according to the present invention may cover the predetermined object by the covering member to inhibit or kill the microorganisms. Therefore, hygienic and safety issues caused by tainting or breeding of microorganisms can be decreased or avoided. In addition, safety and convenience of cleaning and disinfection may be further improved. Accordingly, mental and physical efforts and time needed for manual disinfection and cleaning can be decreased or avoided.

DETAILED DESCRIPTION

Various embodiments will be described below, and those skilled in the art can easily understand spirits and principles of the present invention through the description with reference to the drawings. However, although some specific embodiments are described in detail herein, these embodiments are intended to be illustrative only and are not to be considered in a limiting or exhaustive sense in all respects. Therefore, for those skilled in the art, various changes and modifications of the present invention should be obvious and easily accomplished without departing from the spirits and principles of the present invention.

Figure 1:
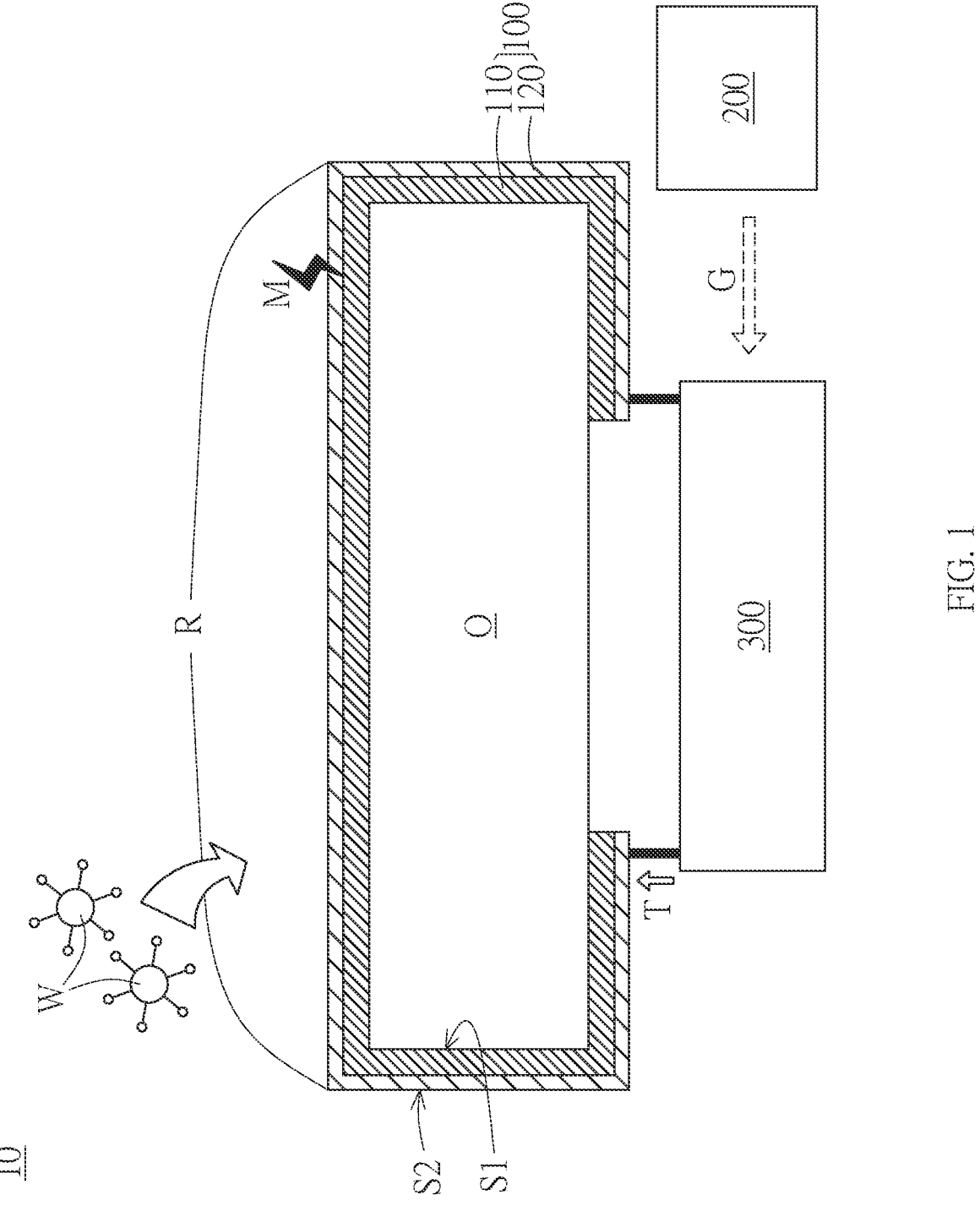
FIG. 1 is a schematic diagram of a microbial inhibition device having a covering member according to an embodiment of the present invention.

Please refer to FIG. 1, according to an embodiment of the present invention, a microbial inhibition device 10 configured to inhibit microorganisms W on a predetermined object O is provided. The microbial inhibition device 10 includes a covering member 100 configured to cover the predetermined object O, a control module 200 configured to issue a control command G, and a power supply module 300 configured to receive the control command G and to power the covering member 100 based on the control command G.

Specifically, the covering member 100 of the microbial inhibition device 10 can be configured to cover or wrap the predetermined object O to decrease or avoid tainting or breeding of the microorganisms W. The covering member 100 may have a shape of thin film or thin layer or any other shape that is convenient to cover the predetermined object O. In addition, the covering member 100 has an attachment surface S1 for attaching to the predetermined object O, and an exposed surface S2 opposite to the attachment surface S1. As such, the attachment surface S1 of the covering member 100 faces the predetermined object O and is not exposed, and the exposed surface S2 is opposite to the predetermined object O and can be exposed to the outside.

In accordance with the present embodiment, the covering member 100 can at least include a conductive medium layer 120. For example, the covering member 100 may include a base layer 110 and the conductive medium layer 120 stacked thereon. The base layer 110 may be any stacked layer to support the conductive medium layer 120, and may be but not limited to made of glass and polymer materials. The conductive medium layer 120 constitutes a predetermined area R of the exposed surface S2. For example, the predetermined area R may correspond to various areas where cleaning and disinfection will be performed such as an area of the predetermined object O on which the microorganisms W taint or breed easily, or an area of the predetermined object O easily and irregularly touched by unspecified individuals, or an area of the predetermined object O which is necessary to be cleaned and disinfected. As such, through the covering member 100 covering the predetermined object O, these areas of the predetermined object O can correspond to the predetermined area R of the exposed surface S2 and can be covered by the predetermined area R to avoid being exposed to the outside.

For example, the conductive medium layer 120 may be formed on the outermost side of the covering member 100 opposite to the predetermined object O and exposed to the outside. Therefore, the predetermined microorganisms W might taint or breed on the conductive medium layer 120, for example, on the predetermined area R of the exposed surface S2, but not limited thereto. Furthermore, the power supply module 300 of the microbial inhibition device 10 may be electrically connected to the conductive medium layer 120. For example, the power supply module 300 may be electrically connected to the conductive medium layer 120 via an electric wire. Based on such a structure, when the control module 200 issues the control command G and it is received by the power supply module 300, the power supply module 300 can power the conductive medium layer 120 based on the control command G. Accordingly, the predetermined microorganisms W is inhibited or killed by conduction. Therefore, tainting and breeding of the predetermined microorganisms W on the area of the predetermined object O corresponding to the predetermined area R can be decreased or avoided.

According to some embodiments, the power supply module 300 can receive electric power via external circuits, or may receive electric power from another module in the microbial inhibition device 10. According to embodiments of the present invention, power source and power supply of modules can be performed via external circuits or other built-in circuits and not elaborated herein.

The conductive medium layer 120 may be powered by the power supply module 300 to be conducted with current T, so as to inhibit or kill the predetermined microorganisms W on the predetermined area R. Specifically, the control command G issued by the control module 200 can reflect a predetermined conduction mode M; hence, the power supply module 300 may power the conductive medium layer 120 based on the control command G in accordance with the predetermined conduction mode M. Therefore, the conductive medium layer 120 can be powered by the power supply module 300 and be conducted with current T in accordance with the predetermined conduction mode M, so as to inhibit or kill the predetermined microorganisms W on the predetermined area R. Specifically, according to the present embodiment, the power supply module 300 can supply the microcurrent T to the conductive medium layer 120 in accordance with the predetermined conduction mode M, for example, predetermined current and predetermined frequency, such that the predetermined microorganisms W on the predetermined area R constituted by the conductive medium layer 120 is acted upon by the microcurrent T, so as to kill or inhibit the predetermined microorganisms W. For example, based on differences in sizes or structures, the predetermined microorganisms W may generate a resonance with specific current and/or specific frequency. As such, biological structure thereof is destroyed or activities thereof are at least decreased. Therefore, hygienic and safety issues which might be caused by the predetermined microorganisms W tainting or breeding on the predetermined object O can be decreased or avoided.

According to some embodiments, the conductive medium layer 120 can be a conductive metal layer, a conductive polymer material layer, or a composite layer thereof, and can be formed by one or more conductive materials. For example, the conductive medium layer 120 can be formed by gold, silver, copper, aluminum, tin, titanium, or combinations thereof. Specifically, the conductive medium layer 120 can be formed by silver, copper, which are not easily tainted by the microorganisms or on which the microorganisms cannot easily breed, or combinations thereof. However, according to different embodiment of the present invention, in the case of having conductivity, materials or patterns of the conductive medium layer 120 are not limited thereto.

Then, according to the predetermined designs, the control module 200 can issue the control command G regularly or in accordance with a predetermined schedule to perform cleaning and disinfection to the predetermined object O regularly or in accordance with the predetermined schedule. Therefore, according to the present embodiment, frequent cleaning and disinfection with low energy consumption can be realized, and the predetermined microorganisms W on the predetermined area R can be inhibited or killed more immediately. Accordingly, the cleaning and disinfection effects on the predetermined object O may be maintained.

Figure 2A:
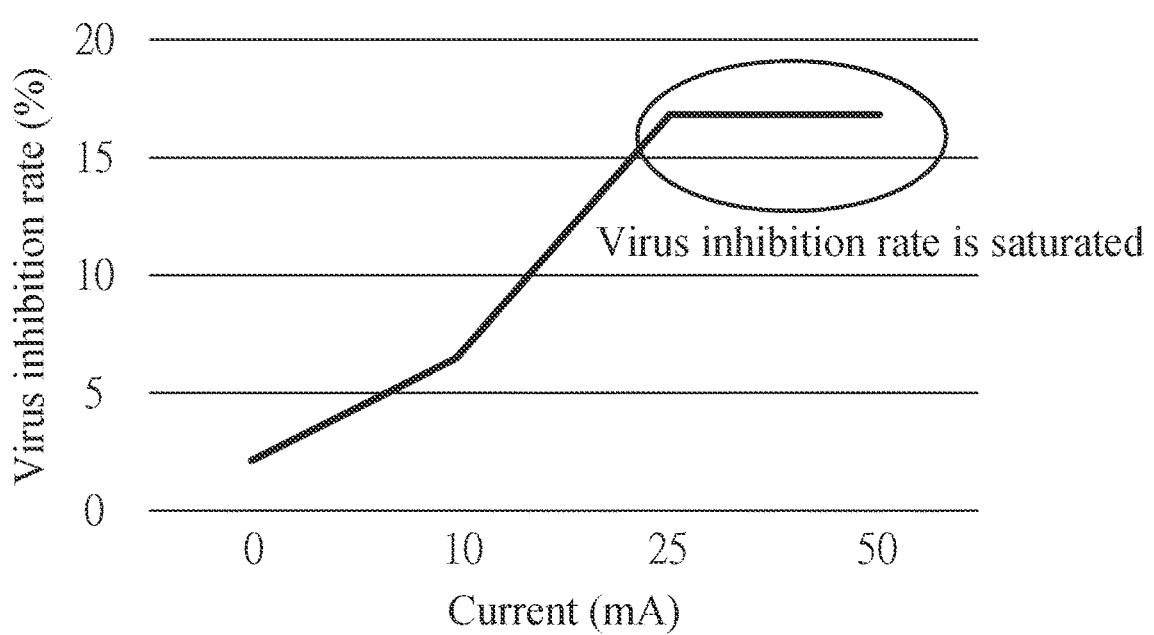
FIG. 2A and FIG. 2B are experimental result graphs of predetermined current and predetermined frequency to specific viruses according to an embodiment of the present invention.

According to embodiments of the present invention, the predetermined conduction mode M can include different conduction patterns such as predetermined current and predetermined frequency. Specifically, the predetermined conduction mode M may be various predetermined currents, predetermined frequencies, and/or the like having effects of inhibiting or killing the predetermined microorganisms W. For example, please refer to FIG. 2A, according to one embodiment, when the predetermined microorganisms W are human coronavirus 229E, and when the current range is micro current without hazard to humans such as 0 to 50 mA, the detected virus inhibition rate (%) may be about 17% saturated within the current range between more than 25 mA and less than or equal to 50 mA. According to such an experimental result, in order to inhibit and kill the human corona virus 229E, based on the consideration of decreasing hazard to humans and decreasing energy consumption, in the predetermined conduction mode M, the conductive medium layer 120 may be conducted with the predetermined current T of 25 mA. However, the present invention is not limited thereto. In addition, the same human corona virus 229E or similar virus having properties of electronic oscillation, in the predetermined conduction mode M, the conductive medium layer 120 can be conducted with the predetermined current T within the range of 10 to 50 mA. For example, in the predetermined conduction mode M, the conductive medium layer 120 can be conducted with the predetermined current T within the range of 20 to 30 mA.

Figure 2B:
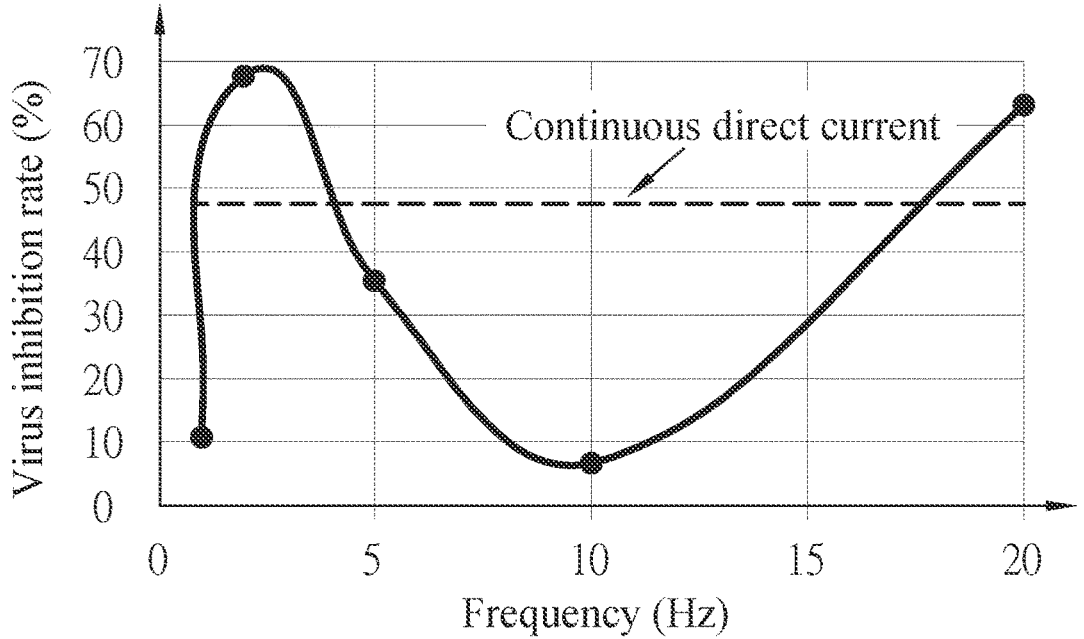

Furthermore, taking the human corona virus 229E for example, referring to FIG. 2B, the conduction to the conductive medium layer 120 based on the predetermined current T of 25 mA can be respectively performed by direct current and alternating current at different frequencies, so as to confirm the mode to provide better effects of inhibiting or killing the specific viruses. As such, according to the present embodiment, when the predetermined microorganisms W are the human corona virus 229E, the detected virus inhibition rate (%) is highest at the predetermined frequency of 2 Hz or 20 Hz. For example, the virus inhibition rate can exceed over 60% and can be close to 70%. As such, the virus inhibition rate of alternating current at the frequency of 2 Hz or 20 Hz is higher than that of alternating current at different frequencies and direct current. Therefore, according to the present embodiment, when the predetermined microorganisms W are the human corona viruses 229E, in the predetermined conduction mode M, the conductive medium layer 120 can be conducted with current at the frequency of 2 Hz or 20 Hz, so as to realize higher virus inhibition rate. For example, the conductive medium layer 120 can be conducted with current at the frequency of 2 Hz. However, other embodiments of the present invention are not limited thereto. In addition, studies and tests can be conducted to various predetermined microorganisms W, so as to confirm the predetermined conduction mode M including the predetermined current, the predetermined frequency and/or the like to provide better effects of inhibiting and killing the predetermined microorganisms W.

As same as the human corona virus 229E, other coronaviruses or corona-like viruses having replicase, spike protein, membrane protein, envelope protein, and nucleocapsid protein can be conducted with current to be inhibited or killed based on the same or similar predetermined conduction mode M. Specifically, spike protein, membrane protein, envelope protein, and nucleocapsid protein are helpful for the viruses to invade human host cells, or they are important structures of protective shells or protective coats of these viruses. As such, inhibition or killing of these viruses can be performed by electrical resonance or electrically destroying these structures. As such, for example, SARS-CoV-2 having spike protein, membrane protein, envelope protein, and nucleocapsid protein can be conducted with current to be inhibited or killed identically or similarly based on the predetermined conduction mode M.

The virus inhibition rate can be measured for example, by conducting current to a copper sheet as the conductive medium layer 120 based on the predetermined conduction mode M after titration arranging a predetermined number of viruses thereon, then comparing cell infection rates thereof to that of the predetermined number of the virus not conducted with current. For example, pulse conduction for different current T can be performed multiple times within a second, so as to test the preferred predetermined current T for inhibiting or killing the viruses. Similarly, conduction for different frequency (e.g. direct current without pulse variation, alternating current at different frequencies with pulse variation) can be performed based on the better predetermined current T, such as 25 mA, within 10 seconds, so as to test the preferred predetermined frequency for inhibiting or killing the viruses.

As such, the predetermined conduction mode M to conduct current to the conductive medium layer 120 may include cross modulation of direct current to perform conduction with the fixed or varying predetermined current T, alternating current at fixed frequency (fixed frequency), alternating current at varying frequency (frequency conversion), or combinations thereof (for example, but not limited to partial fixed frequency and partial varying frequency). Specifically, studies and adjustments can be performed to viruses, bacteria, or organisms to inhibit or kill, so that the predetermined conduction mode M having better effects to inhibit or kill can be performed to the predetermined microorganisms W, or at least cause the predetermined microorganisms W to generate electrical resonance with current conduction during at least a partial period in the predetermined conduction mode M.

According to some embodiments, within the range of micro current that does not damage human bodies, the control module 200 can be controlled in accordance with sizes and structures of the predetermined microorganisms W. As such, the conductive medium layer 120 is provided with current of different frequency and current size, so as to generate resonance or oscillation effects with the predetermined microorganisms W to inhibit activities thereof or kill the predetermined microorganisms W. In addition, the predetermined conduction mode M may also actually include inhibition or killing modes for the different predetermined microorganisms W, so as to inhibit or kill the different predetermined microorganisms W.

Furthermore, according to some embodiments, the conductive medium layer 120 can be designed to have a specific microstructure or a texture style, so as to strengthen conductive effects on specific areas. For example, protruded microstructures can be provided on or around areas of the predetermined object O easily or frequently touched, areas of the predetermined object O on which the predetermined microorganisms W easily or frequently breed, or areas of the predetermined object necessary to keep clean, so as to surround these areas and further increase amounts of conducted current.

In addition, according to some embodiments of the present invention, the covering member 100 of the microbial inhibition device 10 can be positioned to cover the predetermined object O by pasting or clamping. For example, the structures of the covering member 100 can be designed to have a type of interlocking for the predetermined object O to perform cleaning and disinfection. Therefore, the covering member 100 can be directly clamped on the predetermined object O. Or, in order to enhance flexibility of providing the covering member 100, the covering member 100 itself can be designed to have stickiness on the attachment surface S1. As such, it is more convenient and unrestricted to provide the covering member on the various predetermined objects O.

Figure 3:
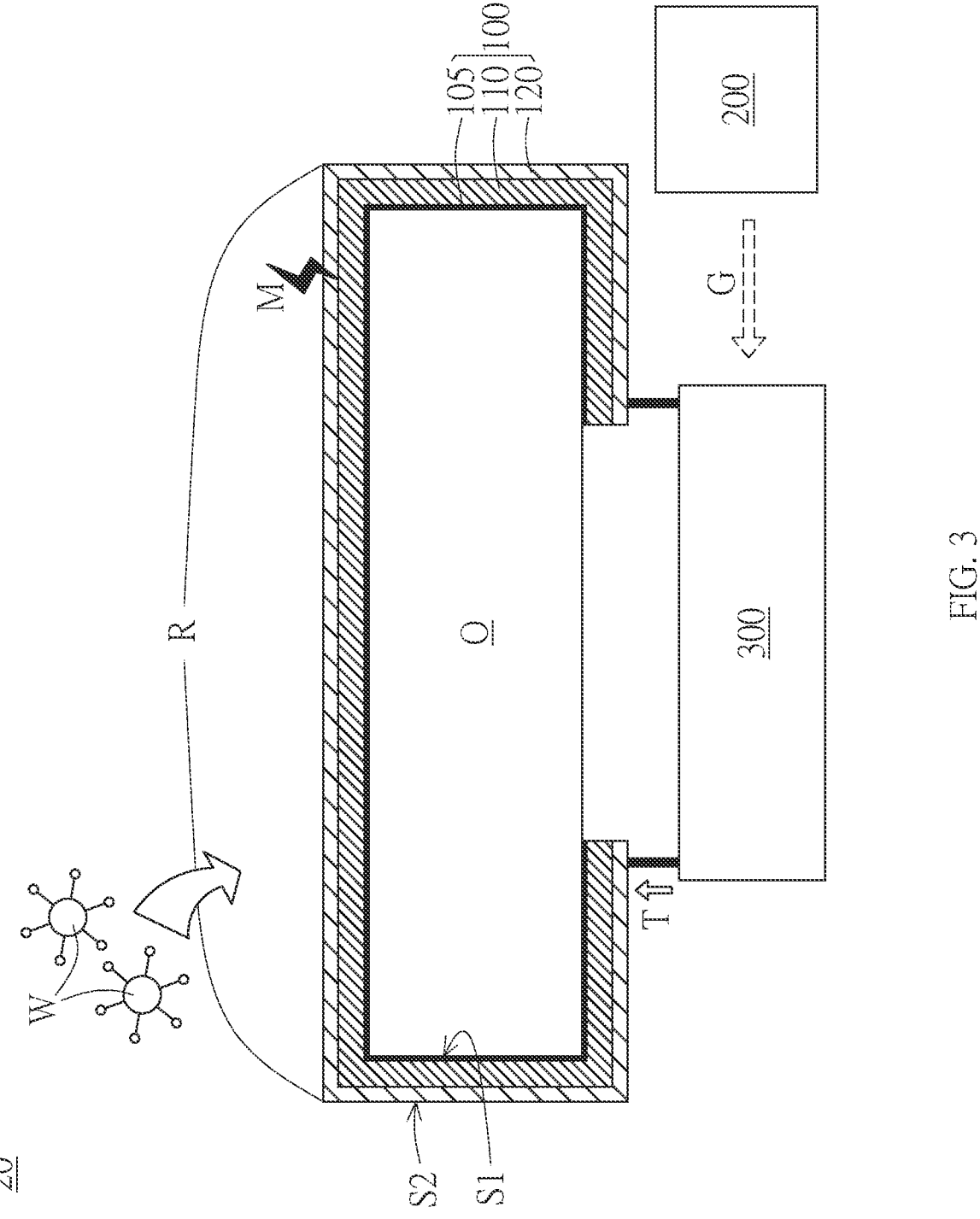
FIG. 3 is a schematic diagram of the microbial inhibition device having a covering member according to another embodiment of the present invention.

For example, with reference to FIG. 3, in the microbial inhibition device 20 according to another embodiment of the present invention, the covering member 100 can further have a colloid 105, so that a portion or an entirety of the attachment surface S1 of the covering member 100 is made of the colloid 105. As such, the covering member 100 can be sticked on the various predetermined objects O through the colloid 105 and conduct current to the conductive medium layer 120 in the predetermined conduction mode M. As such, the predetermined microorganisms W on the predetermined area R corresponding to a portion of the predetermined object O to perform cleaning and disinfection can be inhibited or killed.

In addition to the aforementioned differences, the microbial inhibition device 20 can have structures or configurations same as or similar to the microbial inhibition device 10 above, and it is not elaborated herein.

Figure 4:
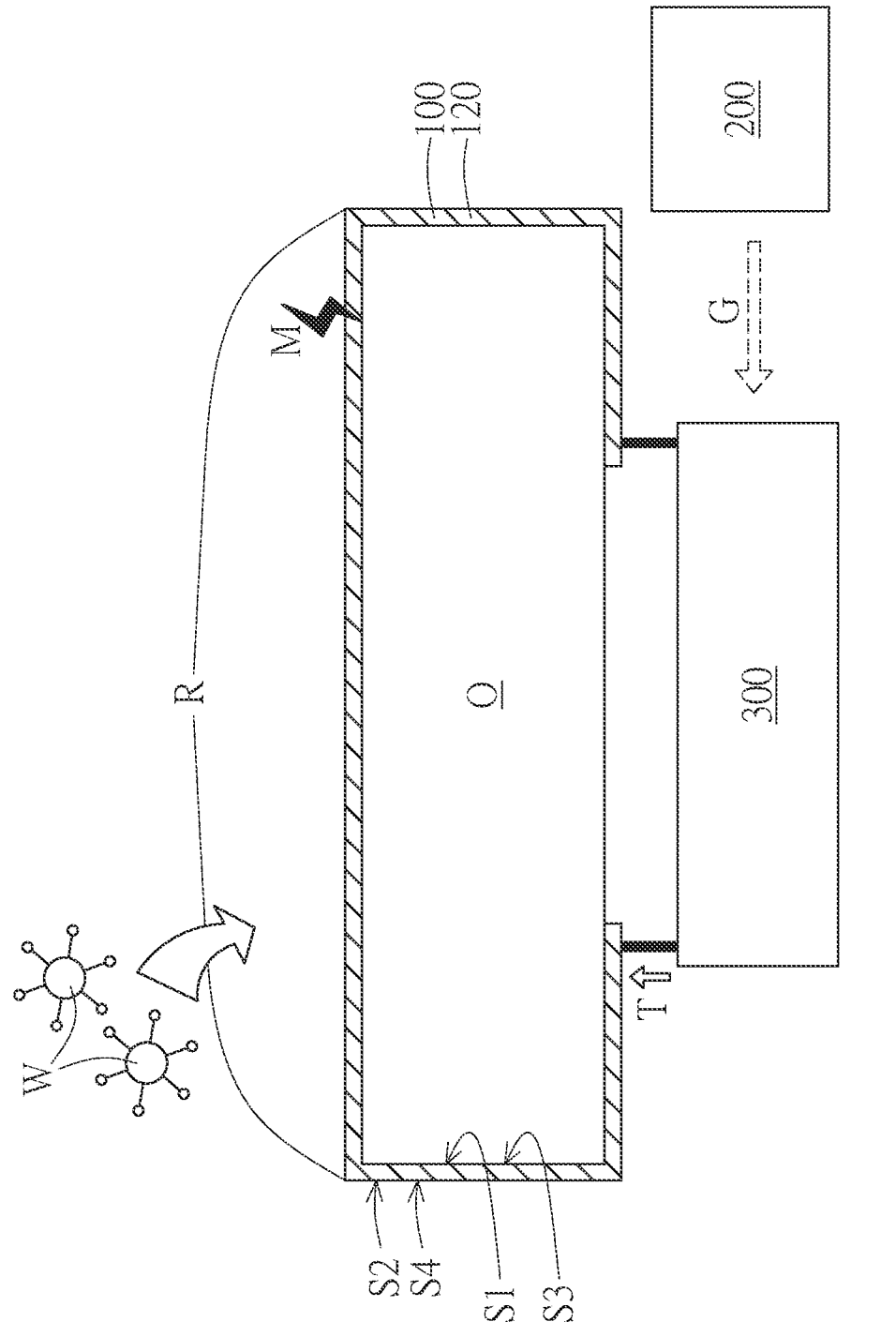
FIG. 4 is a schematic diagram of the microbial inhibition device having a covering member according to yet another embodiment of the present invention.

Furthermore, the type of sticking to the predetermined object O is not limited to the aforementioned patterns. For example, with reference to FIG. 4, in the covering member 100 of the microbial inhibition device 30 according to yet another embodiment of the present invention, the conductive medium layer 120 itself can have stickiness. As such, according to some embodiments, the conductive medium layer 120 may be a conductive polymer material layer or a conductive composite material layer. Therefore, it can be directly sticked to the predetermined object O without further adding the colloid 105.

In the microbial inhibition device 30 according to the present embodiment, the covering member 100 can be only made of the conductive medium layer 120. Since the conductive medium layer 120 itself has stickiness, it is more convenient to stick any one surface of two surfaces thereof to the predetermined object O. For example, according to the present embodiment, the attachment surface S1 and the exposed surface S2 of the covering member 100 can be an inner surface S3 of the conductive medium layer 120 facing the predetermined object O and an outer surface S4 opposite to the predetermined object O, respectively. Actually, the conductive medium layer 120 can also be turned over to be sticked via the opposite surface. Therefore, according to the present embodiment, flexibility of operation can be further enhanced and the conductive medium layer can be sticked on more types of the predetermined object O.

In addition to the aforementioned differences, the microbial inhibition device 30 can have structures and configurations same as or similar to the microbial inhibition device 20 above, and it is not elaborated herein.

According to some embodiments, the covering member 100 may be a member having a fixed shape, or a member formed by soft materials which has flexibility and can be folded. In the case of the covering member 100 being a member having a fixed shape, the reliability and wearability of arranging it on the predetermined object O can be enhanced, so as to extend its service life. On the other hand, in the case of the covering member 100 being a member formed by soft materials which has flexibility and can be folded, the covering member 100 can be molded by matching to the shape of the predetermined object O. Therefore, the range of the predetermined object to which the covering member 100 can be applied can be increased. In addition, the covering member 100 can be molded in accordance with the detailed structures of the predetermined object O to perform closer adhesion, so as to decrease occupied space and obtrusion caused by the covering member 100 provided on the predetermined object O.

As mentioned above, in the microbial inhibition device according to embodiments of the present invention, the control module 200 can issue the control command G (e.g. control signal) to the power supply module 300; and then, the power supply module 300 is configured to conduct current to the conductive medium layer 120 based on the control command. In this regard, the control module 200 can issue the control command G in accordance with the operation. For example, the operators can operate the control module 200 by pressing a button or other ways, for example, but not limited to using a smartphone when the operator thinks that cleaning and disinfection are required. As such, the control module 200 is configured to issue the control command G in accordance with the operation. However, in accordance with other embodiments of the present invention, the control module 200 can also issue the control command G based on a stored or received preset program. Specifically, the control module 200 can have a stored preset program requesting it to issue the control command G regularly or based on the schedule. Or, the control module 200 can receive the preset program from other operation modules, so as to issue the control command G regularly or based on the schedule. Furthermore, the control module 200 can also update or change the preset program by connecting to wired network or wireless network. For example, when a new research result for the predetermined microorganisms W appears or when it is necessary to change the combination of the predetermined microorganisms W to inhibit or kill, the operator can remotely write a new preset program by operating a smartphone, and then transmit it to the control module 200 via Bluetooth and/or the like, so that the control module 200 receives and updates the program. As such, the power supply module 300 is controlled by issuing the control command G regularly or based on the schedule on the basis of the new preset program. People skilled in the art should understand the details thereof and possible modifications, and the contents are not elaborated herein.

Figure 5:
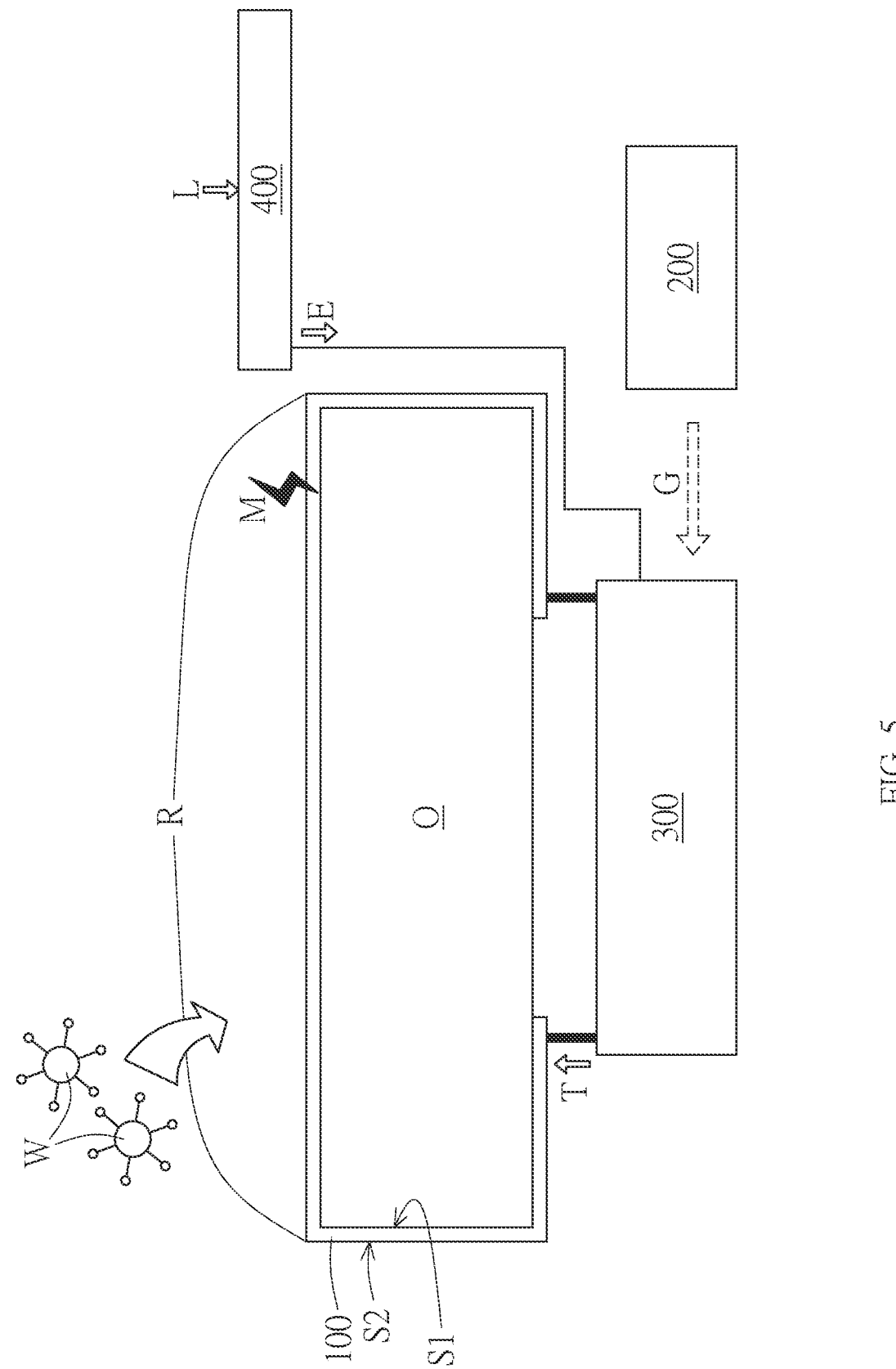
FIG. 5 is a schematic diagram of the microbial inhibition device having a covering member according to a further embodiment of the present invention.

Then, with reference to FIG. 5, according to a further embodiment of the present invention, the microbial inhibition device 40 may have structures or configurations which are similar to or same as the microbial inhibition devices 10, 20, and 30 in each of the aforementioned embodiments. In addition, the covering member 100 is merely illustrated schematically and stacked layers thereof are not specifically illustrated. The microbial inhibition device 40 of the present embodiment can further include a photoelectric conversion module 400 configured to collect light energy L and to convert it to electric power E. For example, the microbial inhibition device 40 can further include the photoelectric conversion module 400 having solar panels. As such the sunlight energy L is collected and converted to the electric power E. As such, the photoelectric conversion module 400 can provide the electric power E to the power supply module 300, so that the power supply module 300 receives the control command G and then conducts current to the conductive medium layer in the covering member 100.

According to the present embodiment, by providing the photoelectric conversion module 400, the microbial inhibition device 40 can generate or supply the required electric power by itself. Therefore, the microbial inhibition device 40 can be provided and applied more conveniently and universally and it is not limited by electric power supplying lines.

Figure 6:
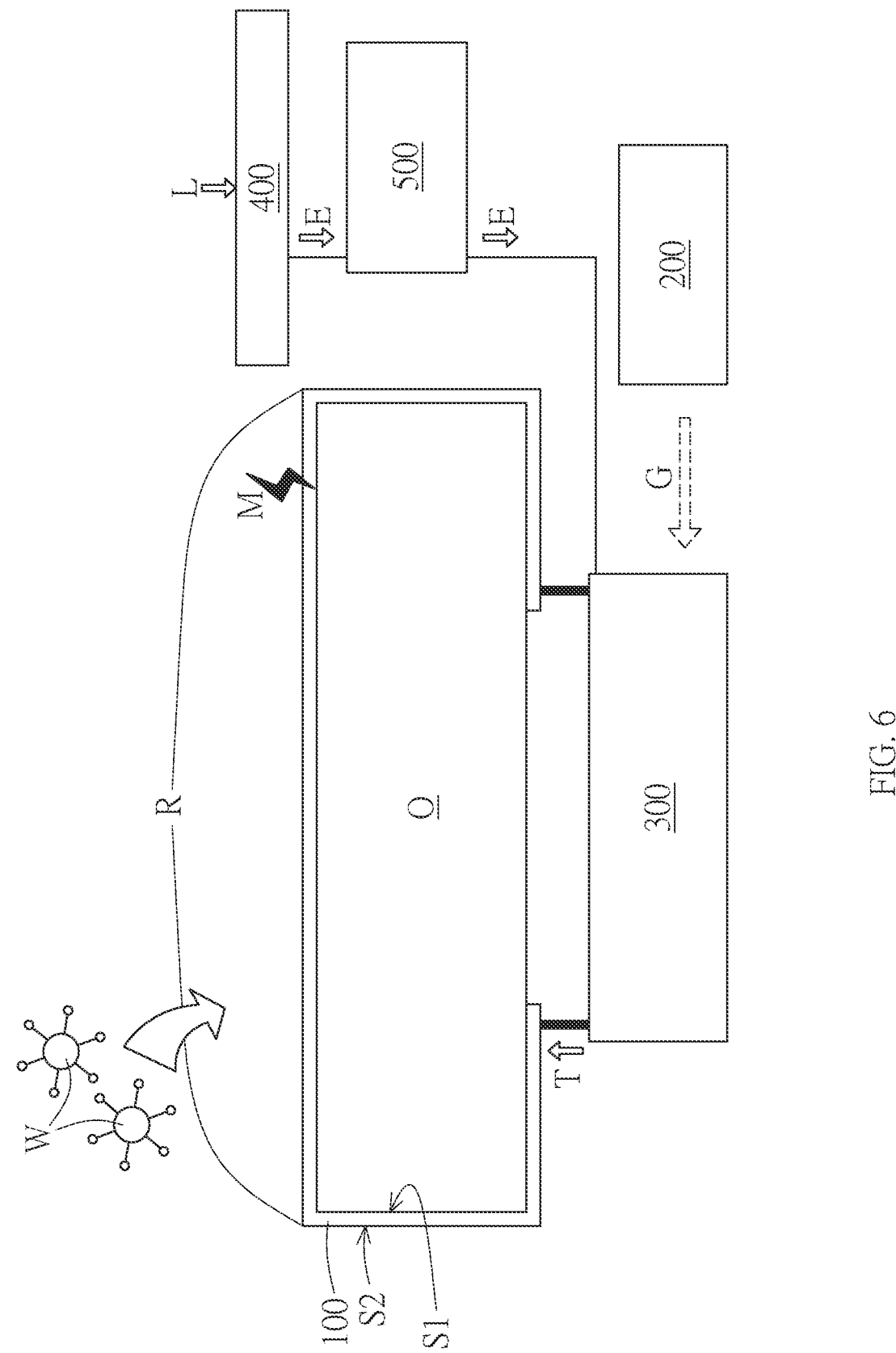
FIG. 6 is a schematic diagram of the microbial inhibition device having a covering member according to another further embodiment of the present invention.

Furthermore, with reference to FIG. 6, according to another further embodiment of the present invention, the microbial inhibition device 50 can have structures or configurations which are similar to or same as the microbial inhibition device 40, and can further include a power storage module 500 such as a rechargeable battery configured to store the electric power E generated by the photoelectric conversion module 400. For example, the microbial inhibition device 50 can store the electric power E converted from the sunlight energy L in the power storage module 500 in the daytime and can allow the power storage module 500 to provide the electric power E to the power supply module 300, so that the power supply module 300 receives the control command G and then conducts current to the conductive medium layer 120. Therefore, according to the present embodiment, in the case of no connection to external power, even if there is no light energy L to collect when it is necessary to perform cleaning and disinfection, it is also possible to make the power supply module 300 receive the control command G and then conduct current to the conductive medium layer in the covering member 100 by the electric power E converted in advance and stored in the power storage module 500. As such, the microbial inhibition device 50 according to the present embodiment can operate on its own, and can further expand the application range and application time of the microbial inhibition device 50.

FIG. 6 illustrates that the photoelectric conversion module 400 is electrically connected to the power storage module 500, and then is electrically connected to the power supply module 300 via the power storage module 500; however, according to other embodiments, the photoelectric conversion module 400 can be also electrically connected to the power storage module 500 and the power supply module 300 at the same time. Therefore, in addition to storing the power in the power storage module 500 and providing the power thereafter, the photoelectric conversion module 400 can directly provide power to the power supply module 300 rather than through the power storage module 500.

In addition, according to other embodiments of the present invention, in addition to the aforementioned modules, more other modules can be further included. For example, an analysis module can be further included to support analyzing the effects or modes of cleaning and disinfection. Different module(s) can be further included in the microbial inhibition device in accordance with the demands to realize more diversified changes, and the contents are not elaborated herein. In addition, the modules can be actually formed by one or more discrete or integrated unit(s), component(s), circuit(s), and/or the like, and the patterns of composing the modules are not limited in the present application. For example, the power supply module 300 and the power storage module 500 can be actually integrated to form one module.

Figure 7:
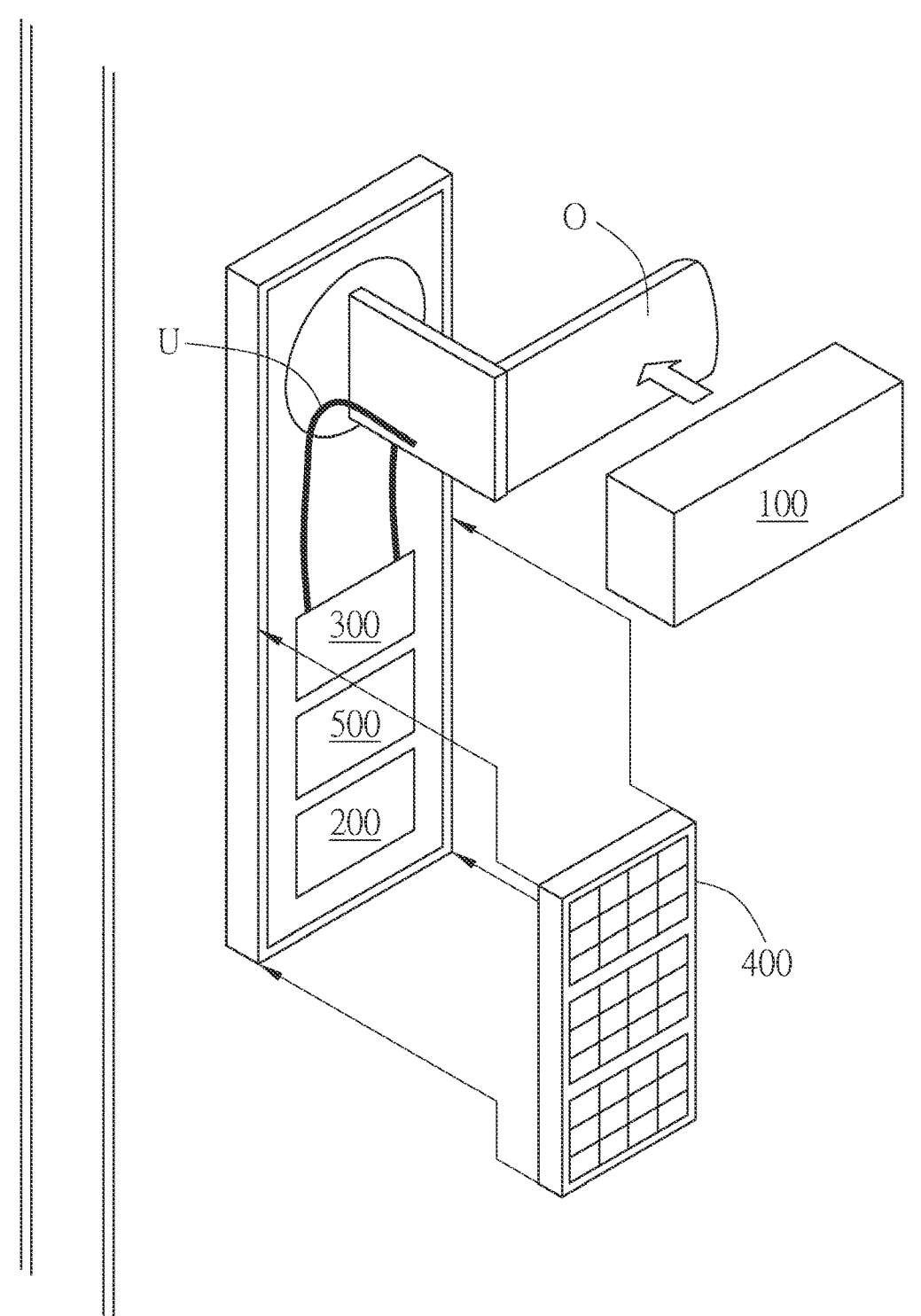
FIG. 7 is a schematic diagram of the microbial inhibition device applied on a doorknob according to an embodiment of the present invention.

Then, please refer to FIG. 7, a microbial inhibition device 60 similar to or same as the microbial inhibition device 50 illustrated in FIG. 6, for example, can be provided on the predetermined object O serving as a doorknob. Specifically, the doorknob is often touched by unspecified individuals; therefore, microorganisms easily taint and breed thereon and are also easily transferred to the next unspecified individual touching the doorknob. Therefore, cleaning and disinfection of the doorknob are important hygienic issues. According to the conventional technology, in order to keep the doorknob clean, it is necessary to often spray alcohol and wipe it relying on manpower. As such, cleaning and disinfection greatly consumes manpower. However, according to the present embodiment, the covering member 100 of the microbial inhibition device 60 can cover the predetermined object O (i.e. the doorknob); therefore, the doorknob is covered up and not exposed. When some individual operates the doorknob, the microorganisms may be on his/her hand and they will taint on the doorknob and further breed thereon. In that case, the power supply module 300 can conduct microcurrent to the conductive medium layer in the covering member 100 based on the control command issued by the control module 200 by electrically connecting the power supply module 300 and the conductive medium layer in the covering member 100 via a circuit U. As such, the microorganisms on the covering member 100 corresponding to the doorknob can be inhibited or killed. Therefore, when the next individual operates the doorknob, it is possible to decrease or avoid the microorganism remained on the doorknob transferring to or infecting people. As such, hygiene and safety of using the doorknob can be improved.

As such, since it is unnecessary to spray alcohol and wipe it by manpower, the microbial inhibition device 60 according to the present embodiment can decrease or avoid frequent manual operations. As such, cleaning and disinfection can be performed more conveniently and quickly. According to the design, frequency and time to perform cleaning and disinfection can be further enhanced and improved.

Furthermore, according to the present embodiment, the photoelectric conversion module 400 and the power storage module 500 can be installed on the door beside the doorknob. As such, the covering member 100 can be powered by directly using the light energy in the environment. Therefore, through the present embodiment, external power lines can be decreased or it is not necessary to provide external power lines. As such, the microbial inhibition device 60 can at least partially or entirely power by itself and automatically perform cleaning and disinfection, so that cleaning and disinfection can be easily maintained. As such, convenience and applicability of the microbial inhibition device 60 can be enhanced and improved.

Figure 8:
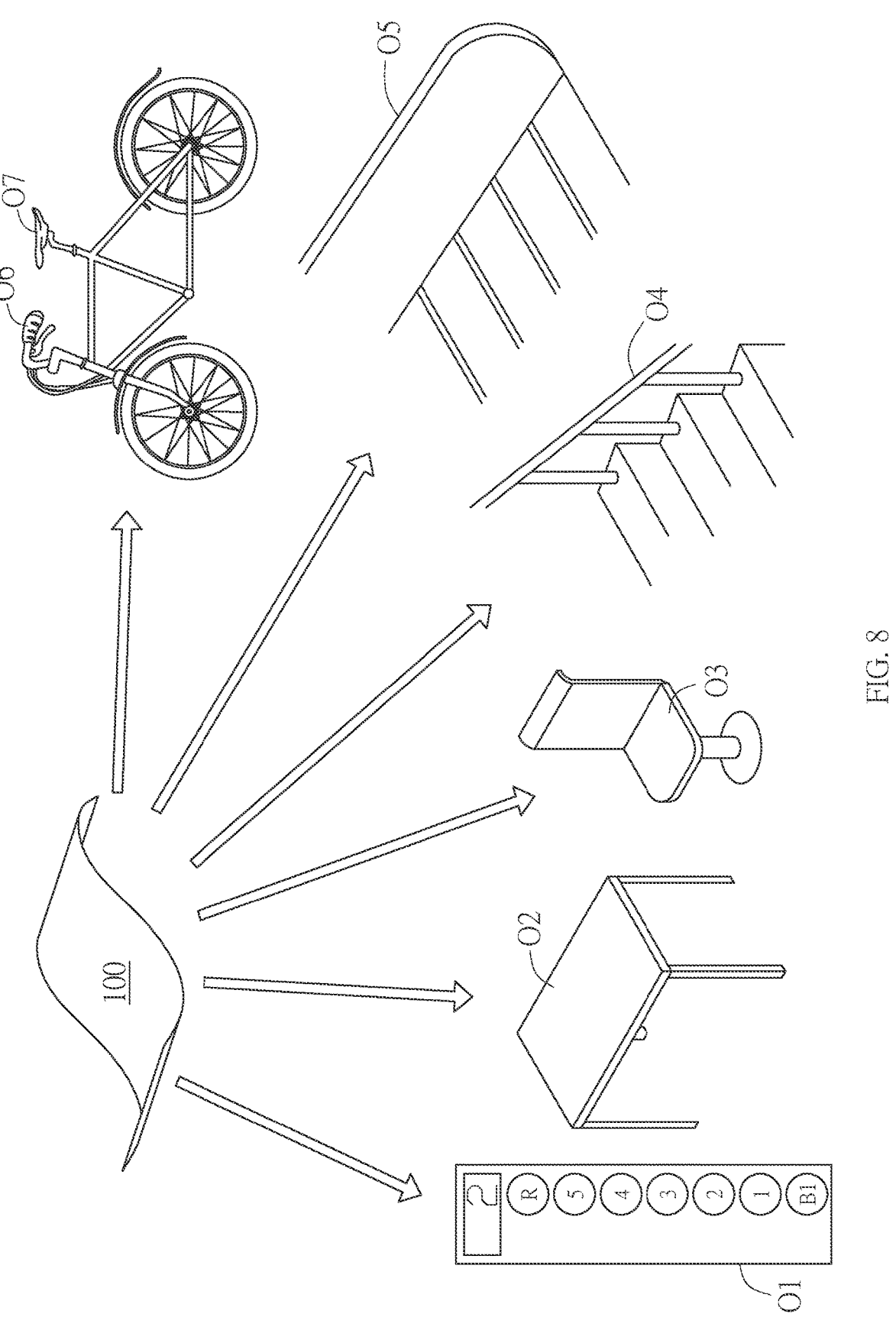
FIG. 8 is a schematic diagram of application scenarios of the microbial inhibition device according to different embodiments of the present invention.

Similarly, according to the present invention, the microbial inhibition devices 10, 20, 30, 40, 50, and 60 in the embodiments above can be provided on various predetermined objects to perform cleaning and disinfection or to maintain hygiene. For example, with reference to FIG. 8, the predetermined objects may include an elevator button O1, a table O2, a chair O3, a stair handle O4, an escalator handle O5, a handle O6 of a vehicle, a seat cushion O7 of a vehicle and/or the like. For example, it can be an object very easily touched by unspecified individuals at variable frequency or time such as a handle or a seat cushion of a rental bicycle. The covering member 100 of in the microbial inhibition device 10, 20, 30, 40, 50, and 60 of the embodiments can be configured to cover these predetermined objects to conduct current to them regularly or in accordance with the predetermined schedule. As such, the predetermined levels of cleaning and disinfection on these predetermined objects can be realized.

However, the predetermined objects above are merely exemplarily, and the objects on which the microbial inhibition device can be installed are not limited thereto according to different embodiments of the present invention. According to other embodiments, a covering member can be provided on any predetermined object to perform cleaning and disinfection, so that cleaning and disinfection are performed by the microbial inhibition device. Accordingly, the predetermined microorganisms W can be killed, the activities of the predetermined microorganisms W can be decreased, or at least risk of spreading and infection of the predetermined microorganisms W can be inhibited. As such, private household sanitation or public environmental sanitation can be improved.

In summary, the microbial inhibition device according to embodiments of the present invention can perform cleaning and disinfection of the predetermined objects without or with decreased manual labor so as to decrease or avoid frequent and repetitive manual operations. In addition, chemical agent residues after completing cleaning and disinfection can be decreased or avoided, and UV light or high temperature which might be result from cleaning and disinfection by UV light or heating can be decreased or avoided; therefore, potential hazards to humans can be further decreased or avoided. Furthermore, energy consumption by using the microbial inhibition device according to embodiments of the present invention is far lower than that of UV light or heating; therefore, efficiency of energy use can be enhanced. In addition, interaction effects between the predetermined objects to perform disinfection and denaturation reaction by heating or UV light can be decreased or avoided; therefore, the microbial inhibition device according to embodiments of the present invention can also make up for some situations in which it is difficult to perform cleaning and disinfection by traditional methods thereof. For example, it can be performed on the object easily damaged due to high temperature or high humidity. Therefore, the microbial inhibition device according to embodiments of the present invention can more flexibly provide the covering member on various predetermined objects as needed, and can perform cleaning and disinfection to the microorganisms (for example, but not limited to routine disinfection to SARS-CoV-2) more flexibly and more specifically. As such, convenience and applicability of cleaning and disinfection can be further enhanced or improved.

The foregoing merely represents some preferred embodiments of the present invention. It will be apparent to people skilled in the art that various modifications and variations can be made to the disclosed embodiments without departing from the scope or spirit of the disclosure. It will be apparent to people skilled in the art that the present invention is defined by appended claims and without departing from the intention of the present invention, various variations such as replacement, combination, modification, and adapting for other purposes and/or the like do not exceed over the scope of the following claims of the present invention.

What is claimed is:

1. A microbial inhibition device for inhibiting microorganisms on a predetermined object, comprising:
   a covering member configured to cover the predetermined object, and having an attachment surface for attaching to the predetermined object, and an exposed surface opposite to the attachment surface, wherein the covering member comprises at least a conductive medium layer, and the conductive medium layer constitutes a predetermined area of the exposed surface;
   a control module configured to issue a control command, the control command instructing a predetermined conduction mode; and
   a power supply module electrically connected to the conductive medium layer, configured to receive the control command, and configured to power the conductive medium layer based on the control command in accordance with the predetermined conduction mode;
   wherein the conductive medium layer is conducted with current in accordance with the predetermined conduction mode through the power supply module, so as to inhibit or kill predetermined microorganisms on the predetermined area.

2. The microbial inhibition device of claim 1, wherein the conductive medium layer is conducted with predetermined current ranging from 10 to 50 mA in the predetermined conduction mode.

3. The microbial inhibition device of claim 2, wherein the conductive medium layer is conducted with predetermined current ranging from 20 to 30 mA in the predetermined conduction mode.

4. The microbial inhibition device of claim 3, wherein the conductive medium layer is conducted with predetermined current of 25 mA in the predetermined conduction mode.

5. The microbial inhibition device of claim 1, wherein the conductive medium layer is conducted with predetermined frequency of 2 Hz or 20 Hz in the predetermined conduction mode.

6. The microbial inhibition device of claim 1, wherein the predetermined microorganisms comprise coronaviruses or corona-like viruses having replicase, spike protein, membrane protein, envelope protein, and nucleocapsid protein.

7. The microbial inhibition device of claim 1, further comprising:
   a photoelectric conversion module configured to collect light energy and to convert it to electric energy, so that the power supply module conducts the conductive medium layer after receiving the control command.

8. The microbial inhibition device of claim 7, further comprising:
   a power storage module configured to store the electric energy generated by the photoelectric conversion module and to provide the electric energy to the power supply module, so that the power supply module conducts the conductive medium layer after receiving the control command.

9. The microbial inhibition device of claim 1, wherein the predetermined conduction mode includes cross modulation of direct current conducting by fixed or varying predetermined current, alternating current at fixed frequency, alternating current at varying frequency, or combinations thereof.

10. The microbial inhibition device of claim 1, wherein the control module is configured to issue the control command in accordance with operations.

11. The microbial inhibition device of claim 1, wherein the control module is configured to issue the control command based on a preset program stored or received.

12. The microbial inhibition device of claim 11, wherein the control module is configured to connect to wired network or wireless network to update or change the preset program.

13. The microbial inhibition device of claim 1, wherein the covering member is positioned and covered on the predetermined object by pasting or clamping.

14. The microbial inhibition device of claim 1, wherein the predetermined microorganisms generate electrical resonance with current conduction during at least a partial period in the predetermined conduction mode.

15. The microbial inhibition device of claim 1, wherein the conductive medium layer is a metal layer, a polymer material layer, or a composite layer thereof.

16. The microbial inhibition device of claim 1, wherein the conductive medium layer is formed by one or more conductive materials.

17. The microbial inhibition device of claim 16, wherein the conductive medium layer is formed by gold, silver, copper, aluminum, tin, titanium, or combinations thereof.

18. The microbial inhibition device of claim 1, wherein the attachment surface of the covering member is an inner surface of the conductive medium layer facing the predetermined object, and the exposed surface of the covering member is an outer surface of the conductive medium layer opposite to the predetermined object.

* * * * *